(12) United States Patent
Kuriyama et al.

(10) Patent No.: US 11,272,092 B2
(45) Date of Patent: Mar. 8, 2022

(54) IMAGING DEVICE, ENDOSCOPE APPARATUS, AND OPERATING METHOD OF IMAGING DEVICE

(71) Applicant: OLYMPUS CORPORATION, Tokyo (JP)

(72) Inventors: Naoya Kuriyama, Tokyo (JP); Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/082,262

(22) Filed: Oct. 28, 2020

(65) Prior Publication Data

US 2021/0044757 A1 Feb. 11, 2021

Related U.S. Application Data

(63) Continuation of application No. PCT/JP2018/019039, filed on May 17, 2018.

(51) Int. Cl.
*H04N 5/00* (2011.01)
*A61B 1/00* (2006.01)
(Continued)

(52) U.S. Cl.
CPC ... *H04N 5/232125* (2018.08); *A61B 1/00006* (2013.01); *A61B 1/00188* (2013.01);
(Continued)

(58) Field of Classification Search
CPC .......... H04N 5/232125; A61B 1/00006; A61B 1/00188
(Continued)

(56) References Cited

U.S. PATENT DOCUMENTS

2010/0283868 A1* 11/2010 Clark ............... H04N 5/232125
348/231.4
2015/0326798 A1 11/2015 Muto et al.
(Continued)

FOREIGN PATENT DOCUMENTS

JP 2006-33242 A 2/2006
JP 2015-216532 A 12/2015
(Continued)

OTHER PUBLICATIONS

Internal Search Report dated Aug. 7, 2018 issued in PCT/JP2018/019039.

*Primary Examiner* — Jeffery A Williams
(74) *Attorney, Agent, or Firm* — Scully, Scott, Murphy & Presser, P.C.

(57) ABSTRACT

An imaging device includes a processor including hardware. The processor is configured to implement controlling a focus position of an objective optical system configured to form an image of a subject on an image sensor, acquiring L×N images per second captured by the image sensor, and combining acquired M images into one extended depth of field image to extend a depth of field, and outputting L extended depth of field images per second. The processor sets one of the M images as a reference image, performs positioning of the other image or images of the M images with respect to the reference image, and combines the thus positioned M images into the one extended depth of field image.

14 Claims, 13 Drawing Sheets

(51) Int. Cl.
*H04N 5/232* (2006.01)
*H04N 5/225* (2006.01)

(52) U.S. Cl.
CPC ............. *H04N 5/232127* (2018.08); *H04N 2005/2255* (2013.01)

(58) Field of Classification Search
USPC .......................................... 348/76
See application file for complete search history.

(56) References Cited

U.S. PATENT DOCUMENTS

2018/0020149 A1    1/2018   Tanimoto
2018/0067296 A1    3/2018   Sugie et al.
2018/0075617 A1    3/2018   Abe et al.

FOREIGN PATENT DOCUMENTS

JP      2017-6330 A    1/2017
JP      2018-11268 A    1/2018
JP      2018-46543 A    3/2018

* cited by examiner

IMAGING DEVICE, ENDOSCOPE APPARATUS, AND OPERATING METHOD OF IMAGING DEVICE

CROSS REFERENCE TO RELATED APPLICATION

This application is a continuation of International Patent Application No. PCT/JP2018/019039, having an international filing date of May 17, 2018, which designated the United States, the entirety of which is incorporated herein by reference.

BACKGROUND

An endoscope apparatus is required to have a depth of field as deep as possible so as not to impede diagnosis and treatment performed by a user. Despite this requirement, however, the endoscope apparatus recently employs an image sensor having a larger number of pixels, which makes the depth of field shallower.

In order to compensate for the shallow depth of field, introduction of an extended depth of field (EDOF) technology, which extends the depth of field, is proposed. For example, in Japanese Unexamined Patent Application Publication No. 2017-6330, a plurality of images is captured by changing a focus position, and in-focus regions in the plurality of images are combined into a combined image. Subsequently, a next image is captured by changing the focus position, and an in-focus region in the next image and the combined image are combined into a combined image. This can extend a depth of field while preventing an increase in an imaging frame rate.

SUMMARY

According to one aspect of the disclosure, there is provided an imaging device, comprising a processor including hardware, the processor being configured to implement: controlling a focus position of an objective optical system configured to form an image of a subject on an image sensor; acquiring L×N images per second captured by the image sensor, where L is an integer of two or greater and N is a number of one or greater; and combining acquired M images into one extended depth of field image to extend a depth of field, where M is an integer greater than N, and outputting L extended depth of field images per second, wherein the processor sets one of the M images as a reference image, performs positioning of the other image or images of the M images with respect to the reference image, and combines the thus positioned M images into the one extended depth of field image.

According to another aspect of the disclosure, there is provided an endoscope apparatus, comprising the above imaging device.

According to another aspect of the disclosure, there is provided an operation method of an imaging device, comprising: controlling a focus position of an objective optical system configured to form an image of a subject on an image sensor; acquiring L×N images per second captured by the image sensor, where L is an integer of two or greater and N is a number of one or greater; and setting one of acquired M images as a reference image, where M is an integer greater than N, performing positioning of the other image or images of the M images with respect to the reference image, combining the thus positioned M images into one extended depth of field image, and outputting L extended depth of field images per second.

DESCRIPTION OF EXEMPLARY EMBODIMENTS

Figure 1:
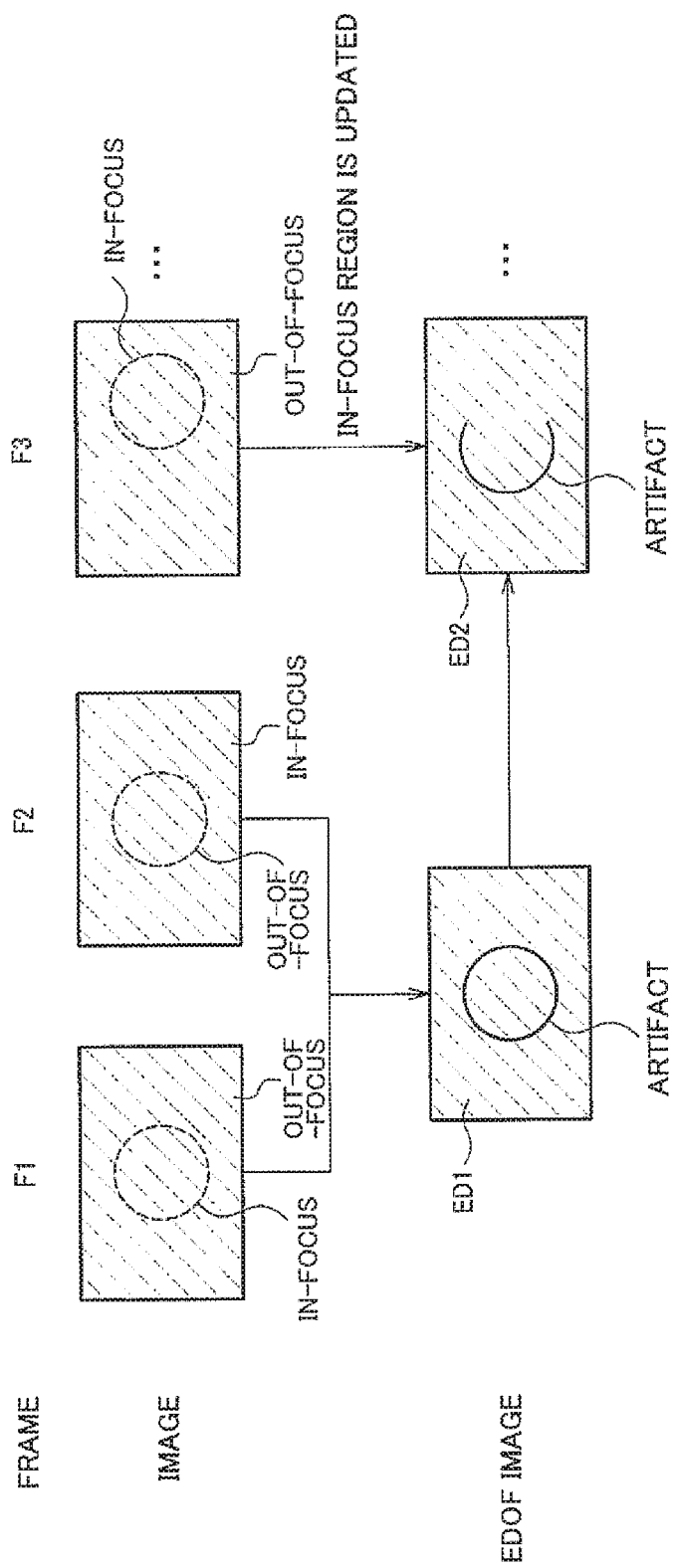
FIG. 1 is a diagram illustrating generation of an artifact in an extended depth of field (EDOF).

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Imaging Device

FIG. 1 is a diagram illustrating generation of an artifact in an extended depth of field (EDOF).

As illustrated in FIG. 1, images in frames F1 and F2 are captured at different focus positions. An inside of a circle indicated by a dotted line is in focus in the frame F1, and an outside of a circle is in focus in the frame F2. In this case, the inside of the circle in the image captured in the frame F1 and the outside of the circle in the image captured in the frame F2 are combined to generate an EDOF image ED1. The dotted line is only for convenience sake and does not actually exist.

Since a plurality of images is combined into the EDOF image ED1, an artifact may occur in the EDOF image ED1.

For example, in a case where brightness of illumination light is changed by lighting control between the frames F1 and F2, the brightness varies between the inside and the outside of the circle that serves as a boundary of the combination, and the uneven brightness becomes an artifact. Or when a subject moves between the frames F1 and F2, the subject is misaligned between the frames and thus the boundary of the combination becomes an artifact. These artifacts do not exist in the actual subject.

Subsequently, an image is captured in a frame F3. A focus position at this time is, for example, the same as the focus position in the frame F1. In the frame F3, an inside of a circle indicated by a dotted line is in focus, and the EDOF image ED1 is updated using this in-focus region to generate an EDOF image ED2. Since the in-focus region in the frame F3 is shifted to the right side from the in-focus region in the frame F1, only a portion of the in-focus region shifted to the right is updated. Thus, the artifact in the EDOF image ED1 disappears partially, but remains in a region that is not updated. Although the updating is similarly repeated thereafter, the artifact never disappears unless the region is updated with an in-focus region. Thus, there is a possibility that the artifact may be displayed for a long period of time.

One of the methods conceived to solve this issue is to generate a new EDOF image every time by combining captured images, instead of updating an EDOF image with another EDOF image. This method, however, poses an issue of decreasing a frame rate of EDOF images or increasing an imaging frame rate. For example, in order to generate an EDOF image from every three frames of captured moving images, and acquire EDOF moving images at 60 frames per second (fps), it is necessary to capture original moving images at 180 fps. Meanwhile, when original moving images are captured at 60 fps and an EDOF image is generated from every three frames, EDOF images are acquired at as low as 20 fps.

As described above, in the conventional technology, it is difficult to quickly update an artifact generated in the EDOF, and to ensure a sufficient frame rate of the EDOF moving images.

Figure 2:
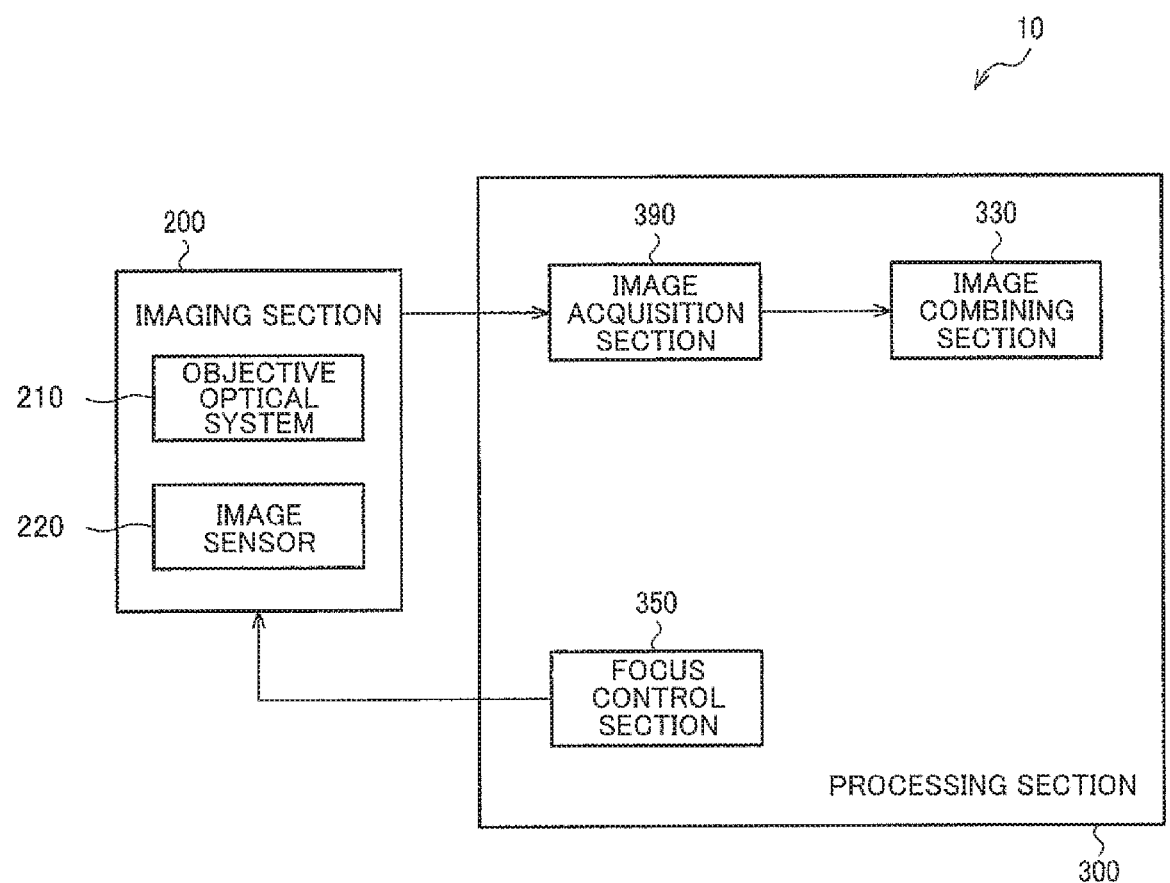
FIG. 2 is a diagram illustrating a configuration example of an imaging device in accordance with the present embodiment.

FIG. 2 is a diagram illustrating a configuration example of an imaging device in accordance with the present embodiment. An imaging device 10 includes a processing section 300 and an imaging section 200. The processing section 300 is, for example, a processing device or a control device. The imaging section 200 is an imager. Note that the imaging section 200 may be detachable.

The imaging section 200 includes an objective optical system 210 and an image sensor 220. The objective optical system 210 forms a subject image on the image sensor 220. While the objective optical system 210 is an objective lens, the objective optical system 210 may further include an optical element such as a prism. The image sensor 220 is an image sensor. The image sensor 220 captures (L×N) images per second. That is, the image sensor 220 captures moving images at a frame rate of (L×N) fps, where L is an integer of two or greater, and N is a number of one or greater. The number of N is a real number which is not limited to an integer, and is, for example, a rational.

The processing section 300 includes a focus control section 350, an image acquisition section 390, and an image combining section 330. The focus control section 350 controls a focus position of the objective optical system 210. The image acquisition section 390 acquires an image captured by the image sensor 220. The image combining section 330 extends a depth of field by combining M images acquired from the image acquisition section 390 into one EDOF image, and outputs L EDOF images per second, where M is an integer greater than N. The image combining section 330 sets one of the M images as a reference image, performs positioning of the other one(s) (non-reference image or images) of the M images with respect to the reference image, and combines the thus positioned M images into one EDOF image.

For example, N=2 and M=3 in FIG. 4 described later. For three images IA1 to IA3, the image combining section 330 sets one image IA2 as the reference image, performs positioning of the other (non-reference) images IA1 and IA3 with respect to the reference image IA2, and combines the thus positioned images IA1 to IA3 into one EDOF image EA1. Subsequently, for three images IA3 to IA5, the image combining section 330 sets one image IA4 as the reference image, performs positioning of the other (non-reference) images IA3 and IA5 with respect to the reference image IA4, and combines the thus positioned images IA3 to IA5 into one EDOF image EA2. Since the frame rate is 120 fps, a relation of (L×N)=120 and L=60 holds. This means that the output frame rate of EDOF images is 60 fps.

In accordance with the present embodiment, M images are combined into an EDOF image, and L EDOF images are output from (L×N) images per second. That is, instead of combining the EDOF image with a newly captured image, the present embodiment combines captured images into an EDOF image. In FIG. 1, where the EDOF image is combined with the newly captured image, an artifact may remain for a long period of time. On the other hand, the present embodiment can shorten an interval of updating an artifact portion even if an artifact is generated.

In accordance with the present embodiment, a relation of N>M leads to a relation of L×N<L×M. This means that EDOF images can be produced while the images to be combined into one EDOF image partially overlap the images to be combined into the subsequent EDOF image. For example, in FIG. 4, the image IA3 is the overlapping image in the EDOF images EA1 and EA2. In a case where the images to be combined into one EDOF image do not overlap the images to be combined into the subsequent EDOF image, the imaging frame rate is (L×M) fps. In contrast, the present embodiment can achieve a lower imaging frame rate of (L×N) fps. That is, this configuration can increase a magnification M of the depth of field, while achieving the imaging at a lowest possible frame rate.

If the positioning is performed in FIG. 1, the positioning is performed between the EDOF image and a newly captured image. In the case where a past positioning has failed, an artifact may remain in the EDOF image. This artifact cannot be eliminated by a later positioning. In this regard, the present embodiment, in which captured images are combined into the EDOF image, enables positioning between the captured images. Hence, the present embodiment can perform the positioning anew every time. Eventually, even if a past positioning has failed, the present embodiment does not leave an artifact due to the failed positioning.

The focus position is a position in focus on a subject side. That is, the focus position is a position of an in-focus plane or a position of an intersection of the in-focus plane and an optical axis. The focus position is represented by a distance from a reference position of the imaging section to the position in focus on the subject side. The reference position of the imaging section is, for example, a position of the image sensor or a position of a distal end of an objective lens. The focus position is adjusted by moving a focus lens in the objective optical system. That is, the focus position and a position of the focus lens correspond to each other, and the focus position can be regarded as the position of the focus lens.

The EDOF image is an image whose depth of field is extended to be greater than the depth of field of the captured image. Specifically, the EDOF image is an image whose depth of field is artificially extended based on a plurality of images having different focus positions. For example, in each local region of an image, an image having the highest focusing degree in the local region is selected from M images, and the local region of the selected image is used to form the EDOF image. The local region is, for example, a pixel. The M images to be combined into the EDOF image in one frame are images sequentially captured by the image sensor.

The focus control section 350 sets the focus position at a different focus position, at a timing of capturing each of the M images.

Figure 4:
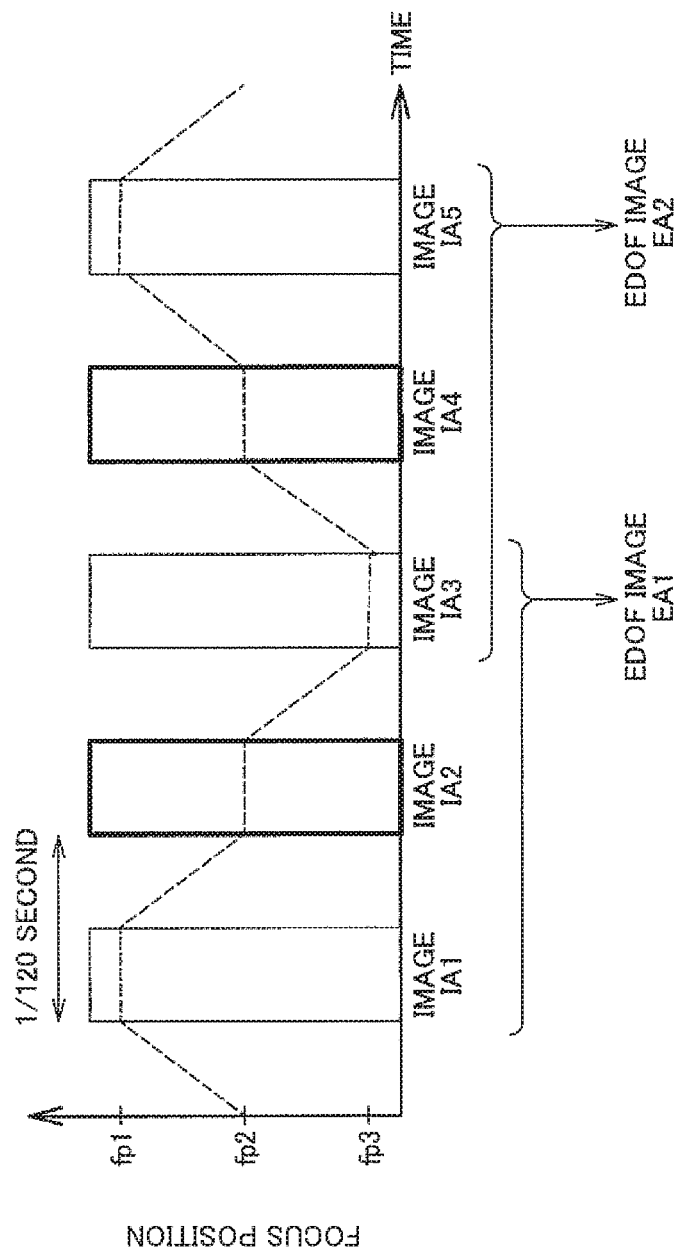
FIG. 4 is a graph illustrating an operation of the endoscope apparatus when N=2 and M=3.

For example, in FIG. 4, the images IA1 to IA3 to be combined into the EDOF image EA1 are combined into the EDOF image EA1. At timings when the images IA1 to IA3 are captured, the focus positions are set to fp1 to fp3, respectively. The focus positions fp1 to fp3 are different from each other.

The present embodiment can extend the depth of field by combining the M images captured at the different focus positions into an EDOF image. Since the present embodiment produces EDOF images while the images to be combined into one EDOF image partially overlap the images to be combined into the subsequent EDOF image, a focus position at a timing of capturing a non-overlapping image is selected from focus positions other than a focus position at a timing of capturing an overlapping image. For example, in FIG. 4, the image IA3 is the overlapping image in the EDOF images EA1 and EA2. Hence, for the images IA3 to IA5 to be combined into the EDOF image EA2, the focus positions fp2 and fp1 at timings of capturing the images IA4 and IA5, respectively, are selected from focus positions other than the focus position fp3 at a timing of capturing the image IA3.

Here, each timing of capturing an image is within an exposure period of the image sensor 220. The timing is, for example, in the middle of the exposure period, but is not limited thereto and may be a freely-selected timing within the exposure period. For example, in FIG. 4, the focus position is at fp1 in the exposure period of the image IA1. While the focus position is set to fp1 in the whole exposure period in FIG. 4, the focus position only needs to be at fp1 at a freely selected timing within the exposure period.

Assume that the focus position includes first to M-th focus positions, the first focus position is a focus position at which the farthest subject is in focus, and the M-th focus position is a focus position at which the nearest subject is in focus. At this time, the focus control section 350 sets the focus position at any one of the second to (M−1)th focus positions at every other timing of capturing an image.

Figure 5:
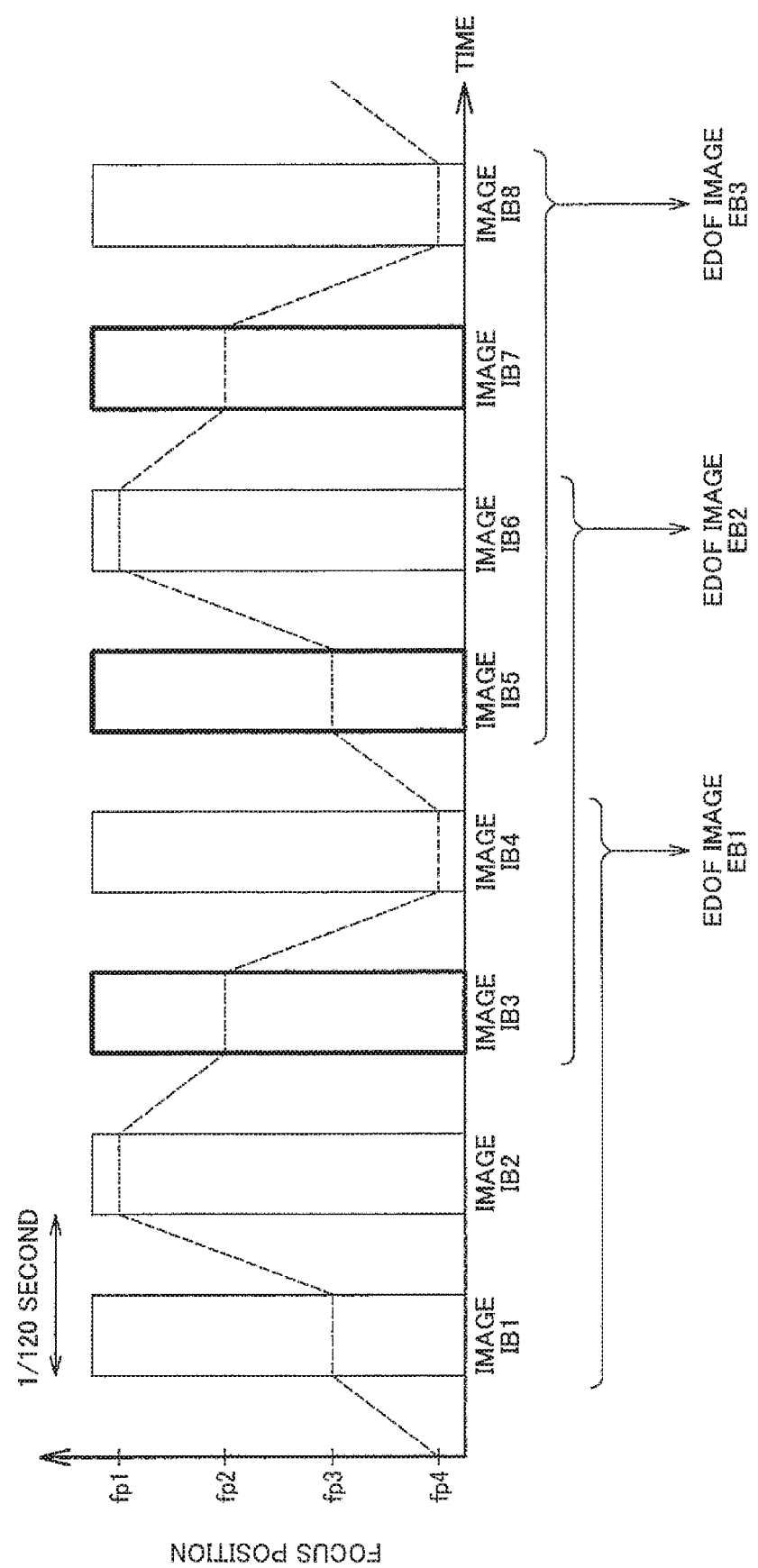
FIG. 5 is a graph illustrating an operation of the endoscope apparatus when N=2 and M=4.

For example, in FIG. 5, the focus position includes focus positions fp1 to fp4, where the focus position fp1 is the focus position at which the farthest subject is in focus, and the focus position fp4 is the focus position at which the nearest subject is in focus. The focus control section 350 sets the focus positions fp3, fp2, fp3, and fp2 at timings of capturing images IB1, IB3, IB5, and IB7, respectively.

An actuator moves the focus position by driving the focus lens. The higher a moving speed of the focus position is, the earlier the actuator deteriorates with age. In this regard, when the focus position is moved from the first focus position to the M-th focus position or from the M-th focus position to the first focus position, the present embodiment sets the focus position on the way, at any one of the second to (M−1)th focus positions. The present embodiment can thus prevent a movement that causes the maximum difference in focus position, and can thereby delay the aged degradation of the actuator.

In this context, N is two, and M is an integer of three or greater and five or less.

Figure 6:
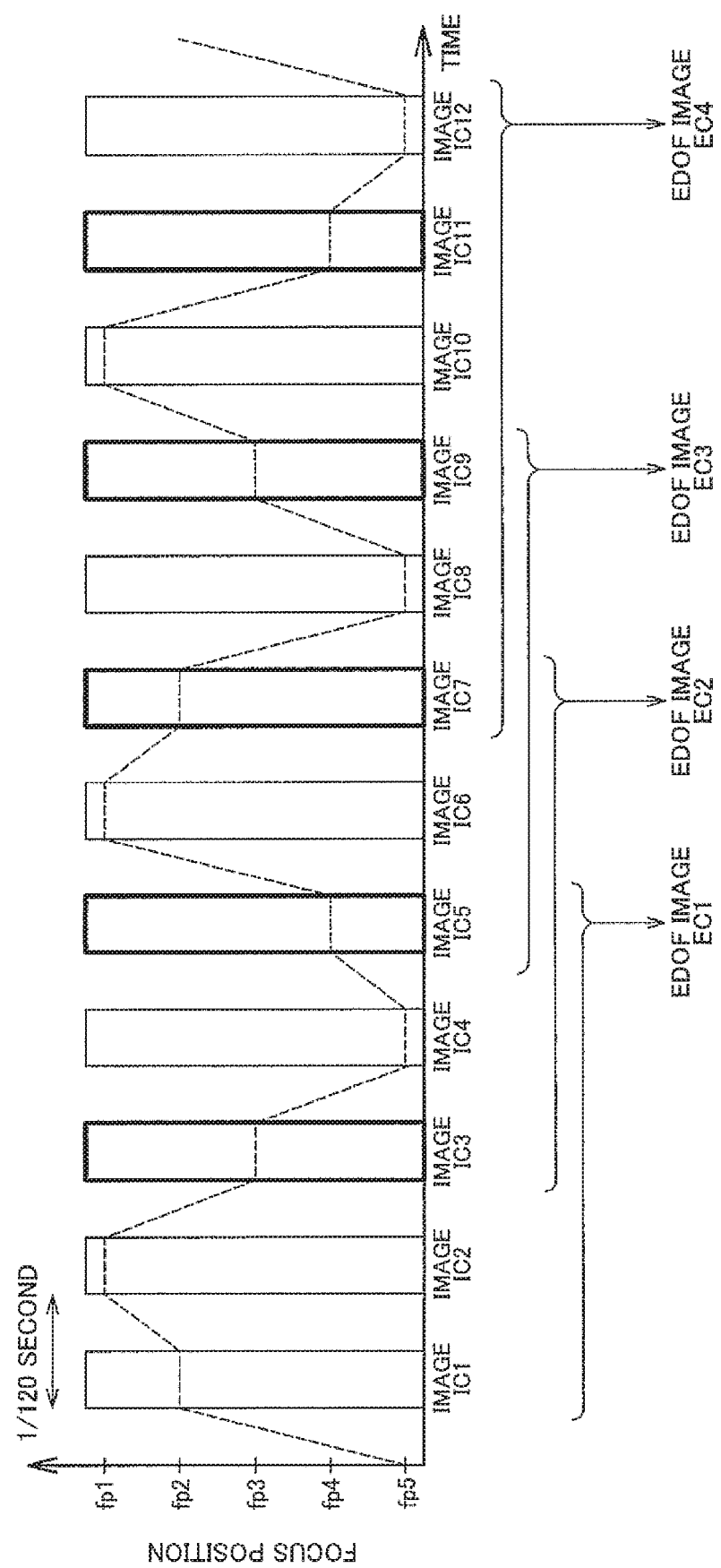
FIG. 6 is a graph illustrating an operation of the endoscope apparatus when N=2 and M=5.

For example, N=2 and M=3 in FIG. 4, N=2 and M=4 in FIG. 5, and N=2 and M=5 in FIG. 6.

In a case where N=2, the images to be combined into an EDOF image are updated two by two. For example, in FIG. 5, images IB1 to IB4 are combined into an EDOF image EB1, and images IB3 to IB6 are combined into an EDOF image EB2. That is, the images IB1 and IB2 are updated with the images IB5 and IB6, respectively, and the images IB3 and IB4 are used in common. In a case where the images are updated two by two, a reference image is preferably set in every two images. In the present embodiment, since any one of the second to (M−1)th focus positions is set in every two images, an image captured at any one of the second to (M−1)th focus positions can be set as the reference image. As a result, the difference in focus position between the images to be subjected to the positioning can be made smaller than the maximum value, which can increase accuracy in positioning. The maximum value is the difference between the first position and the M-th focus position.

At a timing of capturing a next image after capturing an image at the first focus position, the focus control section 350 sets the focus position at any one of the second to (M−1)th focus positions, instead of the M-th focus position. Also, at a timing of capturing a next image after capturing an image at the M-th focus position, the focus control section 350 sets the focus position at any one of the second to (M−1)th focus positions, instead of the first focus position.

As described, when the focus position is moved from the first focus position to the M-th focus position or from the M-th focus position to the first focus position, the present embodiment sets a focus position on the way, at any one of the second to (M−1)th focus positions. The present embodiment can thus prevent a movement that causes the maximum difference in focus position, and can thereby delay the aged degradation of the actuator.

In a case where N is an integer, and suppose that the image acquisition section 390 has acquired the first to (M+N)th images, then the image combining section 330 combines the first to M-th images into a first EDOF image, and combines the (N+1)th to (M+N)th images into a second EDOF image.

For example, N=2 and M=4 in FIG. 5. Out of the images IB1 to IB6, the image combining section 330 combines the images IB1 to IB4 into the EDOF image EB1, and combines the images IB3 to IB6 into the EDOF image EB2.

The present embodiment can extend the depth of field four times (M times), while keeping the frame rate of outputting EDOF images at two times (N times) an imaging frame rate. That is, the present embodiment can extend the depth of field at a high magnification even when imaging is performed at a low frame rate.

When performing the positioning of the first to M-th images, the image combining section 330 sets any one of the first to N-th images as the reference image. The first to N-th images do not overlap the (N+1)th to (M+N)th images to be combined into the second EDOF image.

Figure 7:
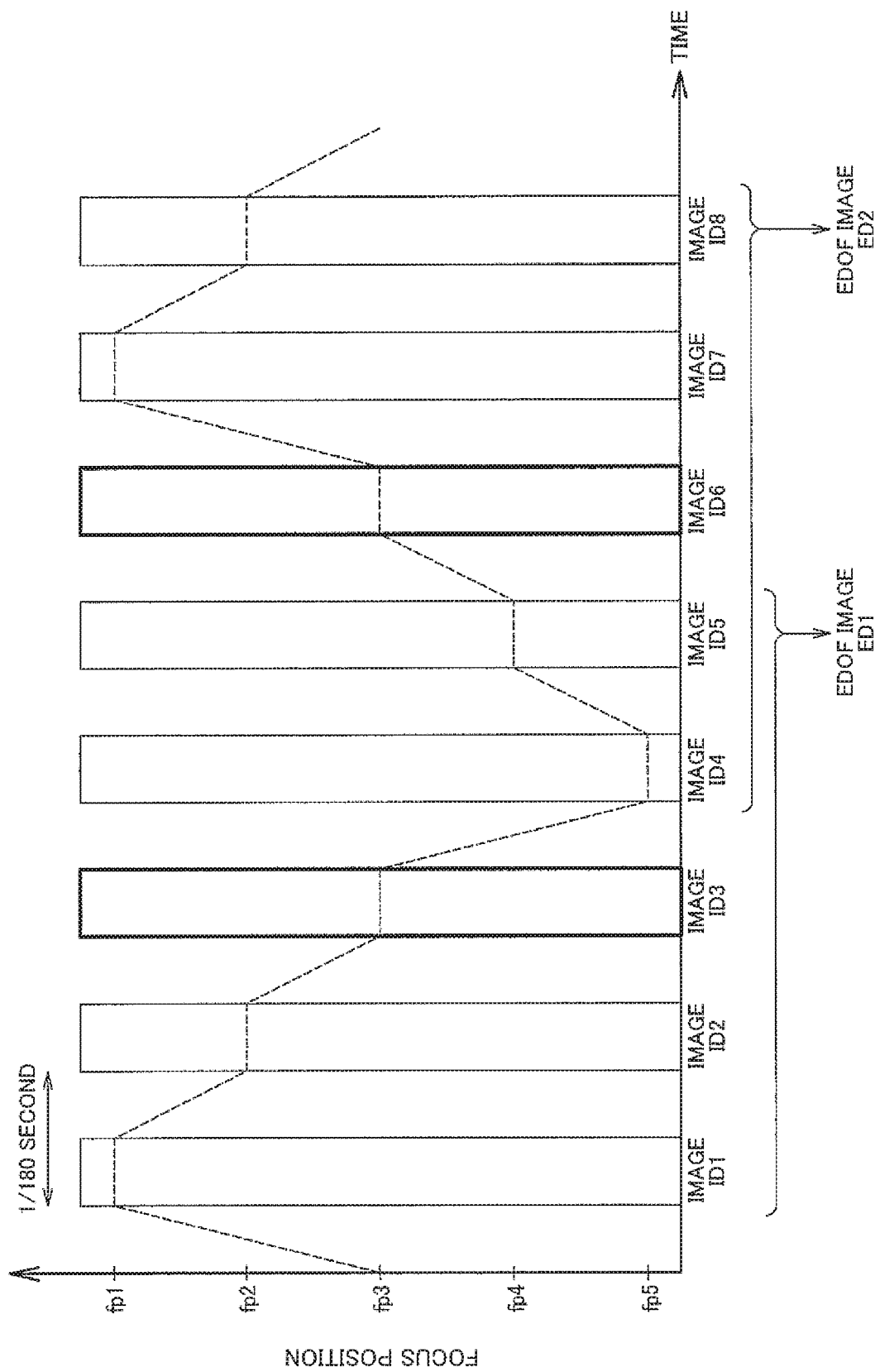
FIG. 7 is a graph illustrating an operation of the endoscope apparatus when N=3 and M=5.

For example, in FIG. 4, the image combining section 330 combines the images IA1 to IA3 into the EDOF image EA1. At this time, the image combining section 330 sets the image IA2 as the reference image for the positioning. The image IA2 does not overlap the images IA3 to IA5 that are combined into the EDOF image EA2 by the image combining section 330. In FIG. 7, the image combining section 330 combines images ID1 to ID5 into an EDOF image ED1. At this time, the image combining section 330 sets the image ID3 as the reference image for the positioning. The image ID3 does not overlap the images ID4 to ID8 that are combined into an EDOF image ED2 by the image combining section 330.

Out of the images combined into an EDOF image, the present embodiment can set a to-be-updated image as the reference image for the positioning. This can reduce a possibility that an artifact remains at the same position. For example, in FIG. 4, the image IA3 is the overlapping image out of the images to be combined into the EDOF images EA1 and EA2, and the overlapping image IA3 is not set as the reference image. In other words, the reference image for combining captured images into the EDOF image EA1 is the image IA2, and the reference image for combining captured images into the EDOF image EA2 is the image IA4. In a case of a moving subject, the position of the subject changes between the image IA2 and the image IA4, and thus the positioning is performed with reference to the different positions of the subject. In this case, an artifact appears at different positions in the EDOF images EA1 and EA2.

Suppose that the image acquisition section 390 has acquired the first to (M+p+q)th images, the image combining section 330 combines the first to M-th images into the first EDOF image, combines the (p+1)th to (M+p)th images into the second EDOF image, and combines the (q+1)th to (M+p+q)th images into a third EDOF image, where p and q are integers of one or greater and less than M, and p is not equal to q. On average, the image combining section 330 outputs L EDOF images per second from (L×N) images.

Figure 9:
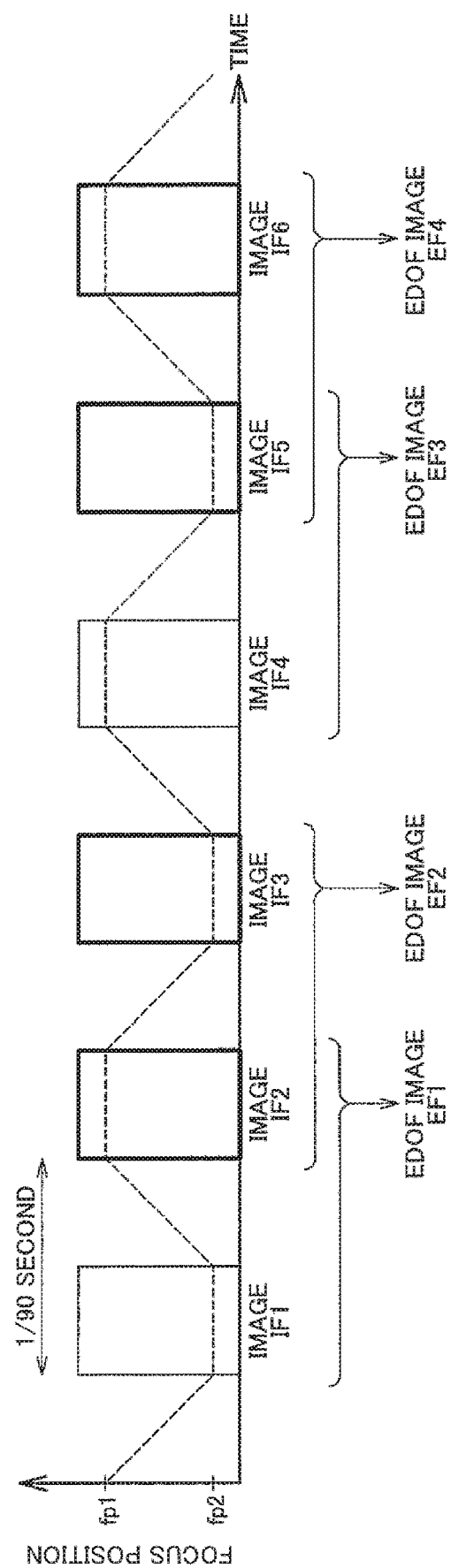
FIG. 9 is a graph illustrating an operation of the endoscope apparatus when N=3/2 and M=2.

For example, M=2, p=1, and q=2, in FIG. 9. Out of images IF1 to IF5, the image combining section 330 combines the images IF1 and IF2 into an EDOF image EF1, combines the images IF2 and IF3 into an EDOF image EF2, and combines the images IF4 and IF5 into an EDOF image EF3. Note that the image combining section 330 does not combine the images IF3 and IF4 into an EDOF image. Alternatively, the image combining section 330 combines the images IF3 and IF4 into an EDOF image, but does not output the EDOF image. In FIG. 9, the imaging frame rate is 90 fps, and EDOF images are output at the frame rate of 60 fps. On average, N=90 fps/60 fps=3/2.

In accordance with the present embodiment, the number of images to be combined into the EDOF image is not constant but variable. Even in such a case, the present embodiment can output L EDOF images from the (L×N) images on average. Since M is greater than N, it is possible to reduce the imaging frame rate while increasing the depth of field to the highest possible magnification.

In addition, a relation of 1<N<2 holds.

Figure 11:
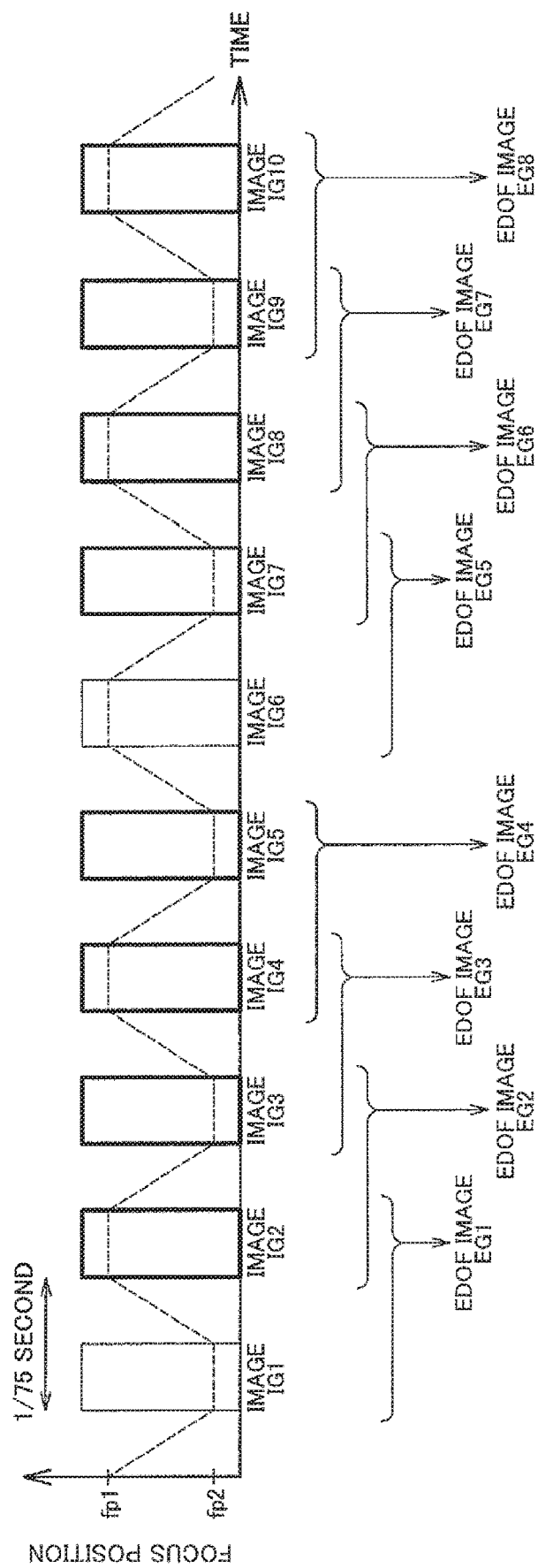
FIG. 11 is a graph illustrating an operation of the endoscope apparatus when N=5/4 and M=2.

For example, N=3/2 in FIG. 9, and N=5/4 in FIG. 11. In addition, M=2 in FIGS. 9 and 11.

When the magnification of the depth of field is expressed as M=2, there are only two focus positions, i.e., fp1 and fp2, which simplifies the selection of the focus position even if the number of updated images changes. That is, the focus position moves simply between the focus positions fp1 and fp2, and the focus positions of consecutive two images are always at fp1 and fp2. When M=2, 1≤N<M=2. When the number of updated images is not constant, 1<N. Namely, a relation of 1<N<2 holds.

The focus control section 350 sets the focus position at any one of the first to M-th focus positions, at a timing of capturing each image. The image combining section 330 sets, as the reference image, an image captured at any one of the second to (M−1)th focus positions.

The difference in focus position is maximum between the first focus position and the M-th focus position. In the present embodiment, an image captured at any one of the second to (M−1)th focus positions can be set as the reference image. As a result, the difference in focus position between the images to be subjected to the positioning can be made smaller than the maximum value, which can increase accuracy in positioning.

The M images to be combined into the EDOF image are the first to M-th images that have been sequentially captured. The image combining section 330 sets any one of the second to (M−1)th images as the reference image.

The difference between image-capturing timings is maximum between a timing of capturing the first image and a timing of capturing the M-th image. The present embodiment can set an image captured at any one of the second to (M−1)th focus positions as the reference image. As a result, the difference in image-capturing timing between the images to be subjected to the positioning can be made smaller than the maximum value, which can increase accuracy in positioning.

When N is an integer, the image combining section 330 sets the reference image at intervals of N images.

If the reference images are not set at regular intervals, the movement of the subject in these reference images is captured at irregular intervals. Since the EDOF image is positioned with reference to the reference image, the position of the subject is the position of the subject in the reference image. When N is an integer, the frame rate of the EDOF images is constant, but the frame rate of the movement of the subject is not constant. In this regard, the present embodiment, which sets the reference image at intervals of the N images, ensures a constant frame rate of the movement of the subject in the EDOF images.

Note that the imaging device 10 in accordance with the present embodiment may be configured as described below. That is, the processing section 300 includes a memory that stores information, and a processor that operates based on the information stored in the memory. The information is, for example, a program and various kinds of data. The processor performs focus control processing, image acquisition processing, and image combining processing. The focus control processing is to control a focus position of the objective optical system that forms a subject image on the image sensor. The image acquisition processing is to acquire (L×N) images per second captured by the image sensor. The image combining processing is to extend the depth of field by combining M images acquired by the image acquisition section into one EDOF image, and to output L EDOF images per second. The image combining processing is to set one of the M images as the reference image, to perform positioning of the other (non-reference) image or images of the M images with respect to the reference image, and to combine the thus positioned M images into one EDOF image.

For example, the processor may implement functions of the respective sections by individual hardware or by integrated hardware. For example, the processor includes hardware, and the hardware can include at least one of a circuit that processes a digital signal and a circuit that processes an analog signal. For example, the processor can be composed of one or more circuit devices mounted on a circuit board, or one or more circuit elements. The circuit device is, for example, an integrated circuit (IC) or the like. The circuit element is, for example, a resistor, a capacitor or the like. The processor may be, for example, a central processing unit (CPU). Note that the processor is not limited to the CPU, but may be any of various other processors such as a graphics processing unit (GPU) and a digital signal processor (DSP). The processor may be a hardware circuit that includes an application specific integrated circuit (ASIC). The processor may include an amplifier circuit, a filter circuit, or the like that processes an analog signal. The memory may be a semiconductor memory such as a static random-access memory (SRAM) and a dynamic random-access memory (DRAM), or may be a register. The memory may be a magnetic storage device such as a hard disk drive, or may be an optical storage device such as an optical disk device. For example, the memory may store a computer-readable instruction. A function of each section of the processing section 300 is implemented as a process when the processor executes the instruction. The instruction may be an instruction set that is included in a program, or may be an instruction that instructs the hardware circuit included in the processor to operate. The processing section 300 includes the image acquisition section 390, the image combining section 330, and the focus control section 350, a control section 340, and a preprocessing section 310.

Each section of the processing section 300 in accordance with the present embodiment may be implemented as a module of a program that operates on the processor. For example, the focus control section 350 is implemented as a focus control module, the image acquisition section 390 is implemented as an image acquisition module, and the image combining section 330 is implemented as an image combining module.

Furthermore, the program implementing the process performed by each section of the processing section 300 in accordance with the present embodiment can be stored, for example, in a computer-readable information storage medium. The information storage medium can be implemented by an optical disk, a memory card, a hard disk drive (HDD), or a semiconductor memory, for example. The semiconductor memory is, for example, a read-only memory (ROM). The processing section 300 performs various kinds of processing of the present embodiment based on the program stored in the information storage medium. Thus, the information storage medium stores the program causing a computer to function as each section of the processing section 300. The computer is a device including an input device, a processing section, a storage section, and an output section. The program causes the computer to execute the process of each section of the processing section 300.

2. Endoscope Apparatus

While a description will be given of a case where the imaging device in accordance with the present embodiment is an endoscope apparatus, the imaging device is not limited to the endoscope apparatus. The imaging device only needs to sequentially acquire EDOF images, and for example, only needs to capture EDOF moving images. The imaging device may be, for example, a microscope.

Figure 3:
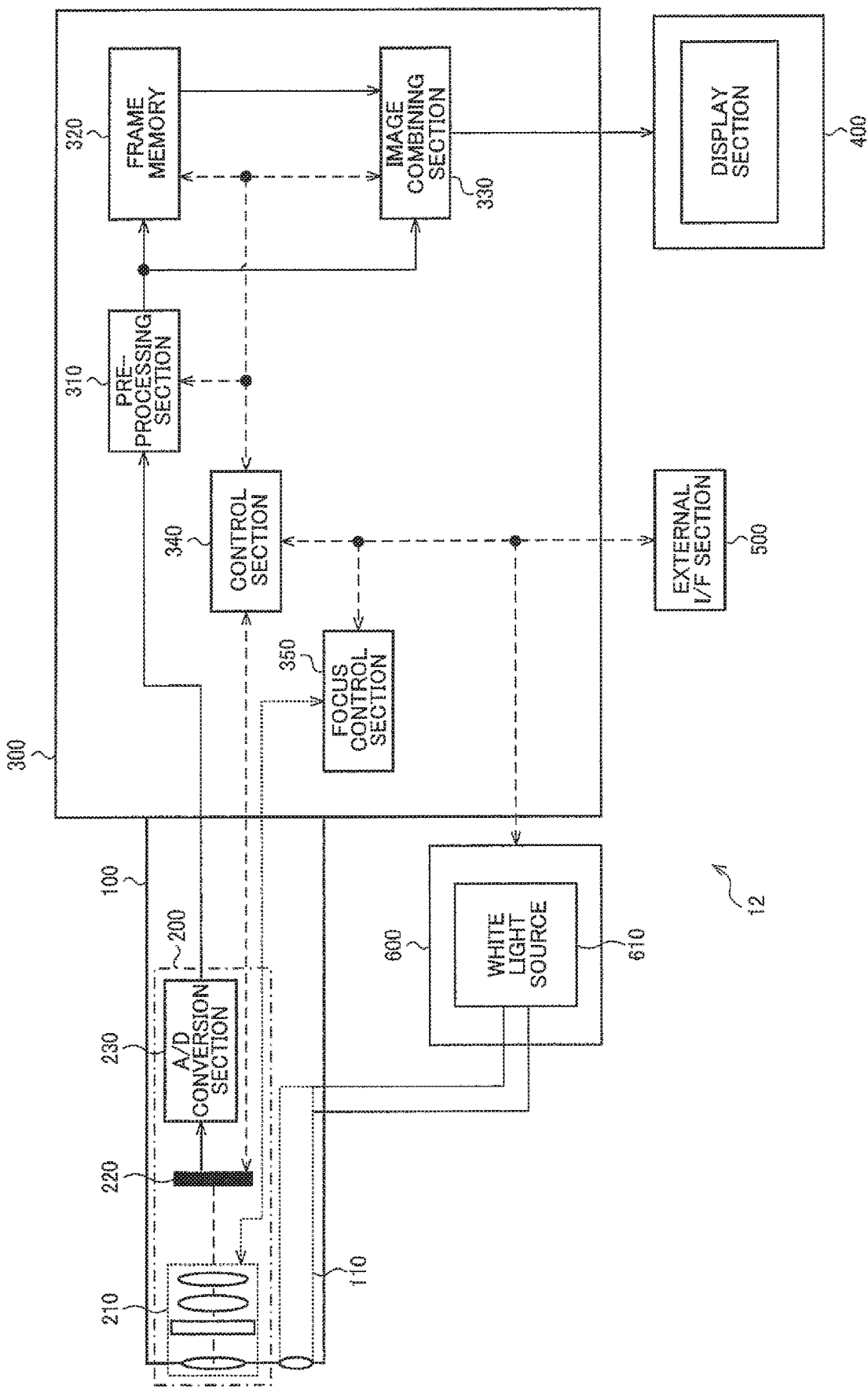
FIG. 3 is a diagram illustrating a detailed configuration example of an endoscope apparatus.

FIG. 3 is a detailed configuration example of an endoscope apparatus 12. The endoscope apparatus 12 illustrated in FIG. 3 is an example of the imaging device 10. The endoscope apparatus 12 includes an insertion section 100, the processing section 300, a display section 400, an external I/F section 500, and an illumination section 600. The insertion section 100 is, for example, a scope. The display section 400 is, for example, a display device. The external I/F section 500 is, for example, an interface, an operation section, or an operation device. The illumination section 600 is, for example, an illumination device or a light source. The endoscope apparatus 12 is, for example, a flexible scope used for a digestive tract or the like, or a rigid scope used for a laparoscope or the like.

The insertion section 100 is inserted into the body. The insertion section 100 includes a light guide 110 and the imaging section 200.

The light guide 110 guides light emitted from the illumination section 600 to a distal end of the insertion section 100. The illumination section 600, for example, includes a white light source 610 and emits white illumination light. The white light source 610 is, for example, a light-emitting diode (LED) or a xenon lamp. The illumination light is not limited to white light, and may be light of various bands available for the endoscope apparatus.

The imaging section 200 forms an image of reflected light from the subject to capture an image of the subject. The imaging section 200 includes the objective optical system 210, the image sensor 220, and an analog to digital (A/D) conversion section 230. The A/D conversion section 230 is, for example, an A/D conversion circuit. Note that the A/D conversion section 230 may be integrated in the image sensor.

Light emitted from the light guide 110 reflects on the subject. The objective optical system 210 receives the reflected light from the subject and forms an image as a subject image. The focus position of the objective optical system 210 is variable and is controlled by the focus control section 350 described later.

The image sensor 220 captures an image by photoelectrically converting the subject image formed by the objective optical system 210. While the image sensor 220 sequentially outputs analog signals to the A/D conversion section 230, the A/D conversion section 230 converts the analog signals into digital images and sequentially outputs the digital images to the preprocessing section 310. Specifically, the image sensor 220 shoots a video of the subject. The A/D conversion section 230 performs A/D conversion of the images in respective frames of the video and outputs digital images to the preprocessing section 310. The preprocessing section 310 outputs a digital video.

The processing section 300 performs signal processing including the image processing and controls the endoscope apparatus 12. The processing section 300 includes the preprocessing section 310, a frame memory 320, the image combining section 330, the control section 340, and the focus control section 350. The preprocessing section 310 is, for example, a preprocessing circuit. The frame memory 320 is, for example, a memory such as a random-access memory (RAM). The image combining section 330 is, for example, an image combining circuit. The control section 340 is, for example, a control circuit or a controller. The focus control section 350 is, for example, a focus control circuit or a focus controller.

The preprocessing section 310 performs the image processing on the images sequentially output from the A/D conversion section 230, and sequentially outputs the resultant images to the frame memory 320 and the image combining section 330. The image processing is, for example, white balance processing, interpolation processing or the like. Note that the preprocessing section 310 in FIG. 3 corresponds to the image acquisition section 390 in FIG. 2.

The frame memory 320 stores (M−1) images output from the preprocessing section 310, and outputs the stored images to the image combining section 330, where M is an integer of two or greater. In this context, one image means an image captured as one frame of a video.

The image combining section 330 combines the (M−1) images stored in the frame memory 320 and one image output from the preprocessing section 310 into one EDOF image, and outputs the EDOF image. That is, the image combining section 330 combines M images into one EDOF image. The image combining section 330 selects, in each local region of the EDOF image, a best focused image out of the M images, extracts the local region of the selected image, and generates an EDOF image by combining the extracted local regions. The image combining section 330 sequentially generates EDOF images from images in the video captured by the imaging section 200, and thereby produces a video including the EDOF images as frame images.

The control section 340 is bidirectionally connected to the image sensor 220, the preprocessing section 310, the frame memory 320, the image combining section 330, and the focus control section 350 to control these sections. For example, the control section 340 synchronizes the exposure period of the image sensor 220 with the focus position of the objective optical system 210. Alternatively, the control section 340 controls lighting of illumination light. That is, the control section 340 controls the quantity of light of the illumination section 600 based on brightness of the image to keep brightness of the image constant.

The focus control section 350 outputs a focus control signal for controlling the focus position to the objective optical system 210. Details of the focus position control will be described later. The imaging section 200 captures images in M frames at different focus positions, and the image combining section 330 combines the M images into one image. Thus obtained is an EDOF image with an extended depth of field.

The display section 400 sequentially displays the EDOF images output from the image combining section 330. That is, the display section 400 displays the video including the EDOF images as the frame images. The display section 400 is, for example, a liquid crystal display, an electroluminescence (EL) display or the like.

The external I/F section 500 is an interface by which a user performs an input or like operation to the endoscope apparatus. That is, the external I/F section 500 is, for example, an interface for operating the endoscope apparatus, or an interface for setting operations of the endoscope apparatus. For example, the external I/F section 500 includes an adjustment button to adjust a parameter for the image processing.

3. Operation

Operations of the endoscope apparatus 12 will be described below. FIG. 4 is a graph illustrating the operation of the endoscope apparatus 12 when N=2 and M=3. Taking the imaging frame rate as IFR and the frame rate of EDOF images as EFR, a relation of N=IFR/EFR holds. M is the number of images combined into one EDOF image.

As illustrated in FIG. 4, the image sensor 220 sequentially captures the images IA1 to IA5. The frame rate is 120 fps. In FIG. 4, each rectangle indicated by a solid line represents an exposure period. The exposure period is a period when the image sensor 220 is in an exposed state. The exposure state is a state where a pixel stores photoelectrically converted electric charge. The focus control section 350 changes the focus position for each image. Specifically, the focus control section 350 changes the focus position for the images IA1, IA2, IA3, and IA4, respectively, from fp1, to fp2, to fp3, and to fp2, and thereafter repeats the processing in a similar manner.

The focus positions fp1 to fp3 correspond to focus positions fp1 to fpM when M=3. The focus position fp1 is on the farthest side among the focus positions fp1 to fpM. The focus position fp2 is on the nearer side than the focus position fp1. The focus position fpM is on the nearest side among the focus positions fp1 to fpM. Assuming that adjacent focus positions are focus positions fpi and fpi+1, the depth of field at the focus position fpi partially overlaps the depth of field at the focus position fpi+1, where i is an integer of one or greater and M−1 or less.

The image combining section 330 combines the images IA1 to IA3 and outputs an EDOF image EA1. At this time, the image combining section 330 sets the image IA2 captured at the focus position fp2 as the reference image, performs positioning of the images IA1 and IA3 with respect to the image IA2, and combines the thus positioned images IA1 to IA3. In FIG. 4, rectangles indicated by thick solid lines represent the reference images. The image combining section 330 combines the images IA3 to IA5 and outputs an EDOF image EA2. At this time, the image combining section 330 sets the image IA4 captured at the focus position fp2 as the reference image, performs positioning of the images IA3 and IA5 with respect to the image IA4, and combines the thus positioned images IA3 to IA5. As a result, the image combining section 330 can output the EDOF images, depths of field of which are extended three times as much, at 120 fps/2=60 fps.

The images IA1 to IA3 to be combined into the EDOF image EA1 have the image IA3 in common with the images IA3 to IA5 to be combined into the EDOF image EA2. Thus, if inaccurate positioning causes an artifact in a region in which the image IA3 is combined, the artifact may appear at the same position in the EDOF images EA1 and EA2.

In this regard, the present embodiment performs the positioning of the images IA1 to IA3 with reference to the image IA2 when combining the images IA1 to IA3 into the EDOF image EA1, and performs the positioning of the images IA3 to IA5 with reference to the image IA4 when combining the images IA3 to IA5 into the EDOF image EA2. In a case of a moving subject, the position of the subject changes between the image IA2 and the image IA4, and thus the positioning is performed with reference to the different positions of the subject. Eventually, an artifact appears at different positions in the EDOF images EA1 and EA2, so that the artifact is less likely to remain at the same position.

Furthermore, inaccurate positioning may cause generation of an artifact such as a double image, in which the same subject is doubly combined. Typically, the larger the difference in focus position and/or the difference in imaging timing, the more difficult the positioning becomes. A larger difference in focus position makes the positioning more difficult because the same subject is blurred so differently in respective images that the subjects on these images cannot be recognized as the same subject. A larger difference in imaging timing makes the positioning more difficult because the movement of the subject on respective images is so much that the position of the subject between these images are significantly different. For example, in a case where the subject has moved out of one of the images, the positioning is impossible. Or in a case where the subject positions are considerably different between the images, the positioning will require a higher calculation cost.

In this regard, the present embodiment sets the image captured at the focus position fp2 as the reference image. While the difference in focus position is maximum between the focus positions fp1 and fp3, the positioning in the present embodiment is performed between the focus positions fp1 and fp2 and between the focus positions fp2 and fp3. Further, the reference image set in accordance with the present embodiment is the second image in the three captured images to be combined into the EDOF image. Although the difference in imaging timing is maximum between the first image and the third image in the captured images, the positioning in the present embodiment is performed between the first image and the second image in the captured images, and between the second image and the third image in the captured images. For the reasons described above, the configuration allows stable positioning, and can reduce a possible generation of an artifact in the EDOF image.

To change the focus position, part of the objective optical system needs to be driven by the actuator. The change in the focus position from fp1 to fp3 requires faster driving than the change in the focus position from fp1 to fp2. Faster driving accelerates degradation of the actuator with age. The present embodiment performs the driving between the focus positions fp1 and fp2 and between the focus positions fp2 and fp3, and can thereby delay aged degradation of the actuator.

FIG. 5 is a graph illustrating the operation of the endoscope apparatus 12 when N=2 and M=4.

As illustrated in FIG. 5, the image sensor 220 sequentially captures the images IB1 to IB8. The frame rate is 120 fps. The focus control section 350 changes the focus position for the images IB1, IB2, IB3, and IB4, respectively, from fp3, to fp1, to fp2, and to fp4, and thereafter repeats the processing in a similar manner.

The image combining section 330 combines the images IB1 to IB4 and outputs an EDOF image EB1. At this time, the image combining section 330 sets the image IB3 captured at the focus position fp2 as the reference image, performs the positioning of the images IB1, IB2, and IB4 with respect to the image IB3, and combines the thus positioned images IB1 to IB4. The image combining section 330 combines the images IB3 to IB6 and outputs an EDOF image EB2. At this time, the image combining section 330 sets the image IB5 captured at the focus position fp3 as the reference image, performs positioning of the images IB3, IB4, and IB6 with respect to the image IB5, and combines the thus positioned images IB3 to IB6. As a result, the image combining section 330 can output the EDOF images, depths of field of which are extended four times as much, at 120 fps/2=60 fps.

The reference image for combining captured images into the EDOF image EB1 is the image IB3. Between the images IB3 and IB1, the difference in focus position is one, and the difference in imaging timing is two. Between the images IB3 and IB2, the difference in focus position is one, and the difference in imaging timing is one. Between the images IB3 and IB4, the difference in focus position is two, and the difference in imaging timing is one. The reference image for combining captured images into the EDOF image EB2 is the image IB5. Between the images IB5 and IB3, the difference in focus position is one, and the difference in imaging timing is two. Between the images IB5 and IB4, the difference in focus position is one, and the difference in imaging timing is one. Between the images IB5 and IB6, the difference in focus position is two, and the difference in imaging timing is one. While the maximum difference in focus position is four as observed between the focus positions fp1 and fp4, the present embodiment avoids performing the positioning when the difference in focus position is maximum. While the maximum difference in imaging timing is four as observed between the first image and the fourth image in the four captured images to be combined into the EDOF image, the present embodiment avoids performing the positioning when the difference in imaging timing is the maximum. For the reasons described above, the configuration allows stable positioning, and can reduce a possible generation of an artifact in the EDOF image.

When the focus position is changed from fp1 to fp4 or from fp4 to fp1, the actuator is driven at the fastest speed. The present embodiment avoids the situation where the actuator is driven at the fastest speed, and can thereby delay aged degradation of the actuator.

In FIG. 5, the images to be combined into the EDOF image are updated two by two every time the EDOF image is generated by combining these images, the number of images to be updated is not limited thereto. Specifically, the images IB1 to IB4 may be combined into the EDOF image EB1, and the images IB4 to IB7 may be combined into the EDOF image EB2. In this case, updating of one image and updating of three images are repeated alternately. Also in this case, the EDOF images are output at an average frame rate of 60 fps, so that a relation of N=120 fps/60 fps=2 holds.

FIG. 6 is a graph illustrating the operation of the endoscope apparatus 12 when N=2 and M=5.

As illustrated in FIG. 6, the image sensor 220 sequentially captures images IC1 to IC12. The frame rate is 120 fps. The focus control section 350 changes the focus position for the images IC1, IC2, IC3, IC4, IC5, IC6, IC7, IC8, IC9, IC10, IC11, and IC12, respectively, from fp2, to fp1, to fp3, to fp5, to fp4, to fp1, to fp2, to fp5, to fp3, to fp1, to fp4, and to fp5, and thereafter repeats the processing in a similar manner.

The image combining section 330 combines the images IC1 to IC5 and outputs an EDOF image EC1. At this time, the image combining section 330 sets the image IC3 captured at the focus position fp3 as the reference image, performs positioning of the images IC1, IC2, IC4, and IC5 with respect to the image IC3, and combines the thus positioned images IC1 to IC5. The image combining section 330 combines the images IC3 to IC7 and outputs an EDOF image EC2. At this time, the image combining section 330 sets the image IC5 captured at the focus position fp4 as the reference image, performs positioning of the images IC3, IC4, IC6, and IC7 with respect to the image IC5, and combines the thus positioned images IC3 to IC7. As a result, the image combining section 330 can output the EDOF images, depths of field of which are extended five times as much, at 120 fps/2=60 fps.

The reference image for combining captured images into the EDOF image EC1 is the image IC3. Between the images IC3 and IC1, the difference in focus position is one, and the difference in imaging timing is two. Between the images IC3 and IC2, the difference in focus position is two, and the difference in imaging timing is one. Between the images IC3 and IC4, the difference in focus position is two, and the difference in imaging timing is one. Between the images IC3 and IC5, the difference in focus position is one, and the difference in imaging timing is two. The reference image for combining captured images into the EDOF image EC2 is the image IC5. Between the images IC5 and IC3, the difference in focus position is one, and the difference in imaging timing is two. Between the images IC5 and IC4, the difference in focus position is one, and the difference in imaging timing is one. Between the images IC5 and IC6, the difference in focus position is three, and the difference in imaging timing is one. Between the images IC5 and IC7, the difference in focus position is two, and the difference in imaging timing is two. While the maximum difference in focus position is five as observed between the focus positions fp1 and fp5, the present embodiment avoids performing the positioning when the difference in focus position is maximum. While the maximum difference in imaging timing is five as observed between the first image and the fifth image in the five images to be combined into the EDOF image, the present embodiment avoids performing the positioning when the difference in imaging timing is maximum. For the reasons described above, the present embodiment allows stable positioning, and can reduce a possible generation of an artifact in the EDOF image.

When the focus position is changed from fp1 to fp5 or from fp5 to fp1, the actuator is driven at the fastest speed. The present embodiment avoids the situation where the actuator is driven at the fastest speed, and can thereby delay aged degradation of the actuator.

In FIG. 6, the images to be combined into the EDOF image are updated two by two every time the EDOF image is generated by combining these images, the number of images to be updated is not limited thereto. Specifically, the images IB1 to IB4 may be combined into the EDOF image EB1, and the images IB4 to IB7 may be combined into the EDOF image EB2. In this case, updating of one image and updating of three images are repeated alternately. Also in this case, the EDOF images are output at an average frame rate of 60 fps, so that a relation of N=120 fps/60 fps=2 holds.

FIG. 7 is a graph illustrating the operation of the endoscope apparatus 12 when N=3 and M=5.

As illustrated in FIG. 7, the image sensor 220 sequentially captures images ID1 to ID8. The frame rate is 180 fps. The focus control section 350 changes the focus position for the images ID1, ID2, ID3, ID4, ID5, and ID6, respectively, from fp1, to fp2, to fp3, to fp5, to fp4, and to fp3, and thereafter repeats the processing in a similar manner.

The image combining section 330 combines the images ID1 to ID5 and outputs an EDOF image ED1. At this time, the image combining section 330 sets the image ID3 captured at the focus position fp3 as the reference image, performs positioning of the images ID1, ID2, ID4, and ID5 with respect to the image ID3, and combines the thus positioned images ID1 to ID5. The image combining section 330 combines the images ID4 to ID8 and outputs an EDOF image ED2. At this time, the image combining section 330 sets the image ID6 captured at the focus position fp3 as the reference image, performs positioning of the images ID4, ID5, ID7, and ID8 with respect to the image ID6, and combines the thus positioned images ID4 to ID8. As a result, the image combining section 330 can output the EDOF images, depths of field of which are extended five times as much, at 180 fps/3=60 fps.

The reference image for combining captured images into the EDOF image ED1 is the image ID3. Between the images ID3 and ID1, the difference in focus position is two, and the difference in imaging timing is two. Between the images ID3 and ID2, the difference in focus position is one, and the difference in imaging timing is one. Between the images ID3 and ID4, the difference in focus position is two, and the difference in imaging timing is one. Between the images ID3 and ID5, the difference in focus position is one, and the difference in imaging timing is two. The reference image for combining captured images into the EDOF image ED2 is the image ID6. Between the images ID6 and ID4, the difference in focus position is two, and the difference in imaging timing is two. Between the images ID6 and ID5, the difference in focus position is one, and the difference in imaging timing is one. Between the images ID6 and ID7, the difference in focus position is two, and the difference in imaging timing is one. Between the images ID6 and ID8, the difference in focus position is one, and the difference in imaging timing is two. While the maximum difference in focus position is five as observed between the focus positions fp1 and fp5, the present embodiment avoids performing the positioning when the difference in focus position is maximum. While the maximum difference in imaging timing is five as observed between the first image and the fifth image in the five images to be combined into the EDOF image, the present embodiment avoids performing the positioning when the difference in imaging timing is maximum. For the reasons described above, the present embodiment allows stable positioning, and can reduce a possible generation of an artifact in the EDOF image.

When the focus position is changed from fp1 to fp5 or from fp5 to fp1, the actuator is driven at the fastest speed. The present embodiment avoids the situation where the actuator is driven at the fastest speed, and can thereby delay aged degradation of the actuator.

Figure 8:
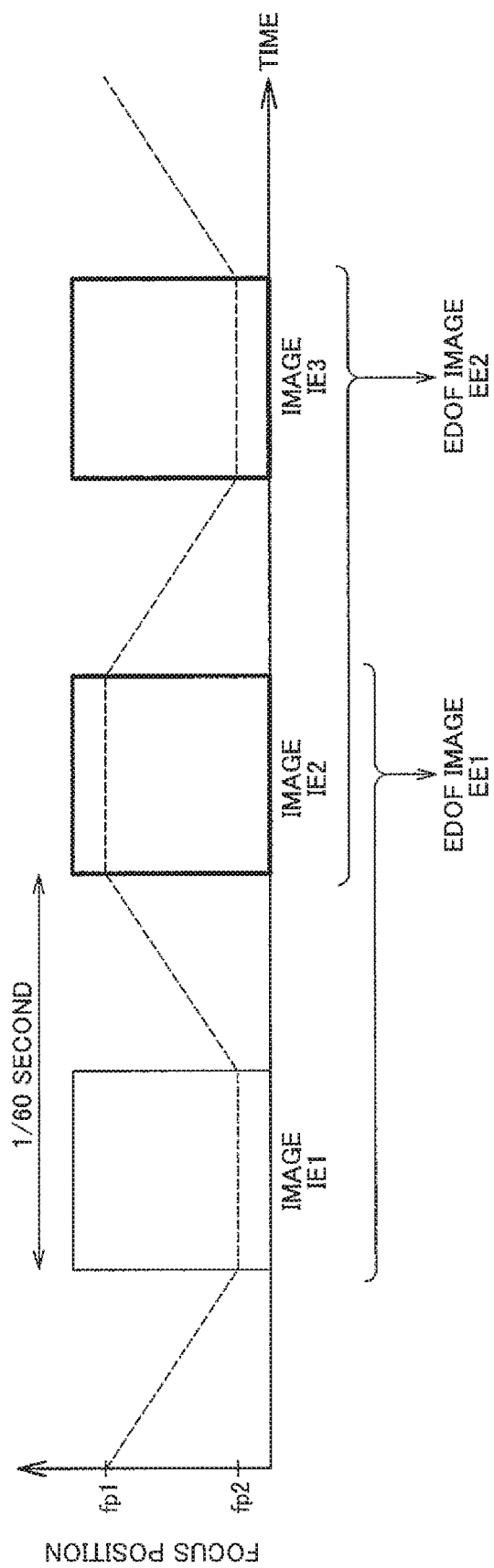
FIG. 8 is a graph illustrating an operation of the endoscope apparatus when N=1 and M=2.

FIG. 8 is a graph illustrating the operation of the endoscope apparatus 12 when N=1 and M=2.

As illustrated in FIG. 8, the image sensor 220 sequentially captures images IE1 to IE3. The frame rate is 60 fps. The focus control section 350 changes the focus position for the images IE1 and IE2, respectively, from fp2 to fp1, and thereafter repeats the processing in a similar manner.

The image combining section 330 combines the images IE1 and IE2 and outputs an EDOF image EE1. At this time, the image combining section 330 sets the image IE2 captured at the focus position fp1 as the reference image, performs positioning of the image IE1 with respect to the image IE2, and combines the thus positioned images IE1 and IE2. The image combining section 330 combines the images IE2 and IE3 and outputs an EDOF image EE2. At this time, the image combining section 330 sets the image IE3 captured at the focus position fp2 as the reference image, performs positioning of the image IE2 with respect to the image IE3, and combines the thus positioned images IE2 and IE3. As a result, the image combining section 330 can output the EDOF images, depths of field of which are extended twice as much, at 60 fps/1=60 fps.

The present embodiment can extend the depth of field twice as much without increasing the imaging frame rate with respect to the frame rate of the EDOF images. Besides, the present embodiment can decrease a difference in imaging timing between images. As a result, the present embodiment can decrease the amount of movement of the subject between images that require the positioning, and thus can reduce the scale of a circuit that detects the amount of movement.

Regarding the values of N and M, the above description of FIGS. 4 to 8 relates to the case where N=2 and 3≤M≤5, or N=3 and M=5, or N=1 and M=2, but the selection of the values of N and M is not limited thereto. That is, in a possible configuration where N≥1 and M>N, M images are combined into an EDOF image, and N images out of the M images are updated when the next EDOF image is generated by combining the images. This configuration can extend the depth of field M times as much. In a case where none of the images to be combined into an EDOF images overlaps any of the images to be combined into another EDOF image, the imaging frame rate needs to be M times as much as the frame rate of the EDOF images. On the other hand, the present embodiment allows a part of the images to be combined into an EDOF image to overlap a part of the images to be combined into another EDOF image, and can therefore keep the imaging frame rate N times (N<M) the frame rate of the EDOF images. Further, the present embodiment has devised the order of changing the focus position and the manner of selecting the reference image, and can therefore reduce an artifact effectively.

Further regarding the value of N, the above description of FIGS. 4 to 8 relates to the case where N is an integer, but N is not necessarily an integer as described below. For example, N may be s/t (i.e., N=s/t), where s and t are integers of one or greater, and s≠t. The following description relates to some cases where 1<N<2.

FIG. 9 is a graph illustrating the operation of the endoscope apparatus 12 when N=3/2 and M=2.

As illustrated in FIG. 9, the image sensor 220 sequentially captures images IF1 to IF6. The frame rate is 90 fps. The focus control section 350 changes the focus position for the images IF1 and IF2, respectively, from fp2 to fp1, and thereafter repeats the processing in a similar manner.

The image combining section 330 combines the images IF1 and IF2 and outputs an EDOF image EF1. At this time, the image combining section 330 sets the image IF2 captured at the focus position fp1 as the reference image, performs positioning of the image IF1 with respect to the image IF2, and combines the thus positioned images IF1 and IF2. The image combining section 330 combines the images IF2 and IF3 and outputs an EDOF image EF2. At this time, the image combining section 330 sets the image IF3 captured at the focus position fp2 as the reference image, performs positioning of the image IF2 with respect to the image IF3, and combines the thus positioned images IF2 and IF3. The image combining section 330 combines the images IF4 and IF5 and outputs an EDOF image EF3. At this time, the image combining section 330 sets the image IF5 captured at the focus position fp2 as the reference image, performs positioning of the image IF4 with respect to the image IF5, and combines the thus positioned images IF4 and IF5. The image combining section 330 combines the images IF5 and IF6 and outputs an EDOF image EF4. At this time, the image combining section 330 sets the image IF6 captured at the focus position fp1 as the reference image, performs positioning of the image IF5 with respect to the image IF6, and combines the thus positioned images IF5 and IF6. As a result, the image combining section 330 can output the EDOF images, depths of field of which are extended twice as much, at 90 fps/(3/2)=60 fps. Similar to the case shown in FIG. 8, the positioning between only two images can reduce the scale of the circuit that detects the amount of movement.

Figure 10:
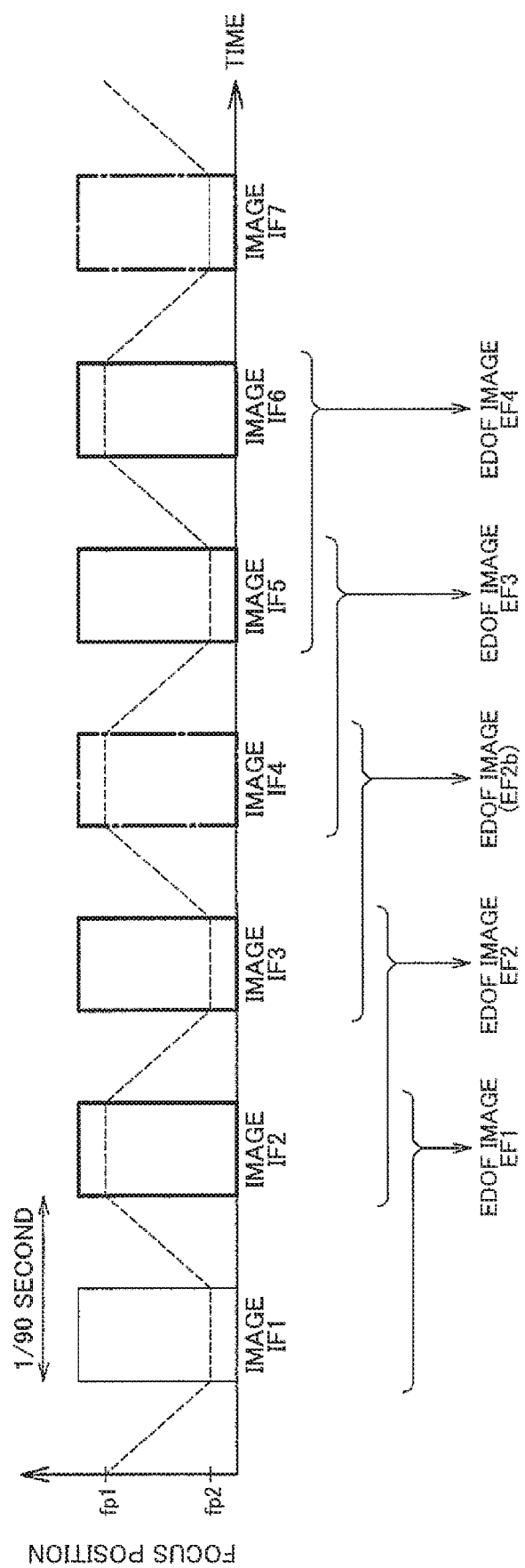
FIG. 10 is a graph illustrating an operation of the endoscope apparatus when N=3/2 and M=2.

In FIG. 9, the image combining section 330 does not combine the images IF3 and IF4 into an EDOF image. Alternatively, as illustrated in FIG. 10, the image combining section 330 may be configured to combine the images IF3 and IF4 into an EDOF image EF2b, but not to output the EDOF image EF2b. Since the image combining section 330 outputs the EDOF images EF1, EF2, EF3, and EF4, the display section 400 displays the same EDOF images as in the case of FIG. 9.

FIG. 11 is a graph illustrating the operation of the endoscope apparatus 12 when N=5/4 and M=2.

As illustrated in FIG. 11, the image sensor 220 sequentially captures images IG1 to IG10. The frame rate is 75 fps. The focus control section 350 changes the focus position for the images IG1 and IG2, respectively, from fp2 to fp1, and thereafter repeats the processing in a similar manner.

The image combining section 330 combines the images IG1 and IG2 and outputs an EDOF image EG1. At this time, the image combining section 330 sets the image IG2 captured at the focus position fp1 as the reference image, performs positioning of the image IG1 with respect to the image IG2, and combines the thus positioned images IG1 and IG2. The image combining section 330 combines the images IG2 and IG3 and outputs an EDOF image EG2. At this time, the image combining section 330 sets the image IG3 captured at the focus position fp2 as the reference image, performs positioning of the image IG2 with respect to the image IG3, and combines the thus positioned images IG2 and IG3. The image combining section 330 combines the images IG3 and IG4 and outputs an EDOF image EG3. At this time, the image combining section 330 sets the image IG4 captured at the focus position fp1 as the reference image, performs positioning of the image IG3 with respect to the image IG4, and combines the thus positioned images IG3 and IG4. The image combining section 330 combines the images IG4 and IG5 and outputs an EDOF image EG4. At this time, the image combining section 330 sets the image IG5 captured at the focus position fp2 as the reference image, performs positioning of the image IG4 with respect to the image IG5, and combines the thus positioned images IG4 and IG5. The image combining section 330 combines the images IG6 and IG7 and outputs an EDOF image EG5. At this time, the image combining section 330 sets the image IG7 captured at the focus position fp2 as the reference image, performs positioning of the image IG6 with respect to the image IG7, and combines the thus positioned images IG6 and IG7. As a result, the image combining section 330 can output the EDOF images, depths of field of which are extended twice as much, at 75 fps/(5/4)=60 fps.

4. Image Combining Section

Figure 12:
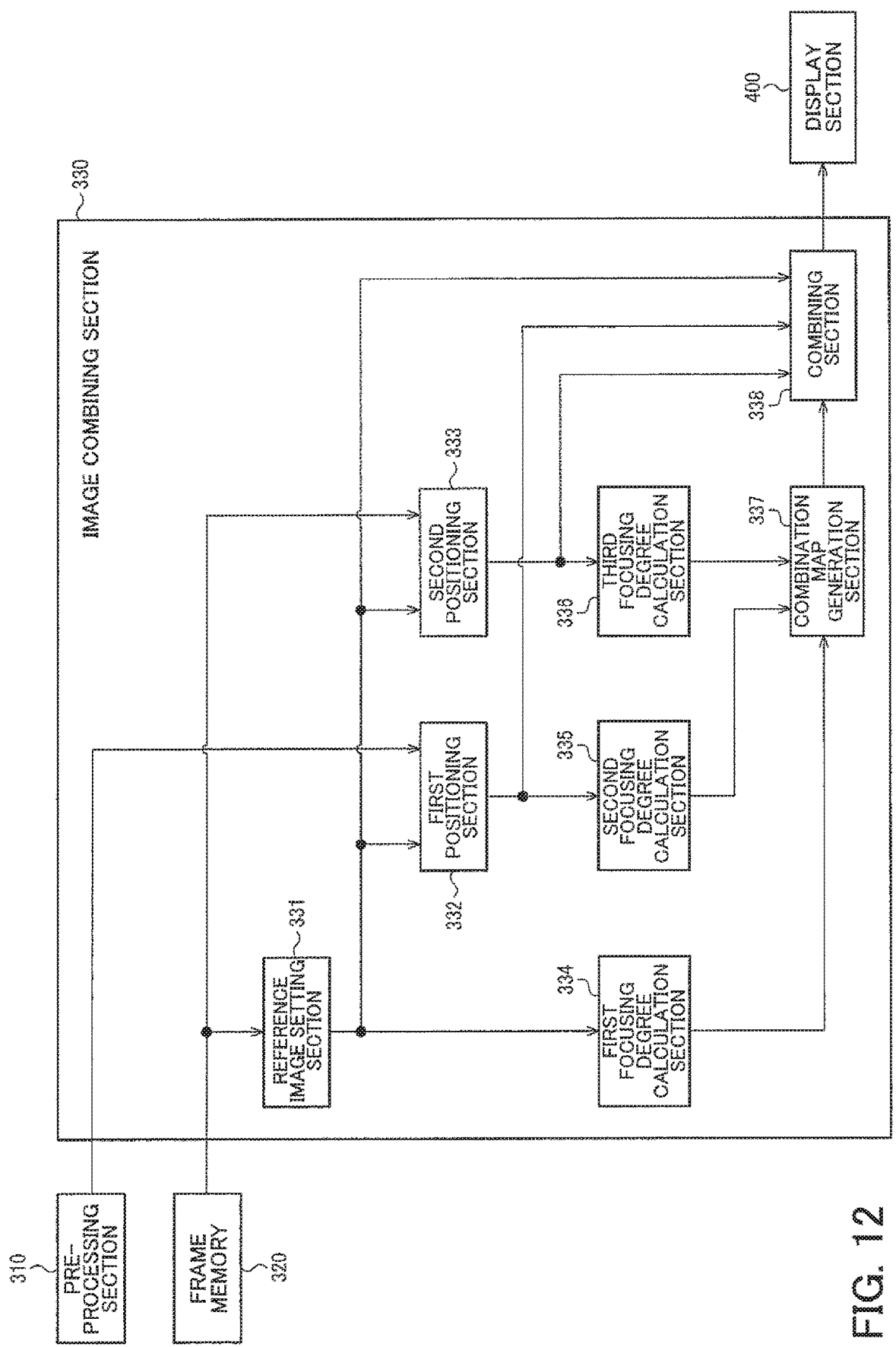
FIG. 12 is a diagram illustrating a detailed configuration example of an image combining section.

A description will be given below of a method of combining images into an EDOF image by the image combining section 330. FIG. 12 is a diagram illustrating a detailed configuration example of the image combining section 330. The image combining section 330 includes a reference image setting section 331, a first positioning section 332, a second positioning section 333, a first focusing degree calculation section 334, a second focusing degree calculation section 335, a third focusing degree calculation section 336, a combination map generation section 337, and a combining section 338. For the purpose of description, M=3 in FIGS. 12 and 13.

The reference image setting section 331 sets one reference image out of two images stored in the frame memory 320. The reference image setting section 331 outputs the set reference image to the first positioning section 332, the second positioning section 333, the first focusing degree calculation section 334, and the combining section 338.

The first positioning section 332 performs pixel-by-pixel positioning of one image output from the preprocessing section 310, with reference to the reference image set by the reference image setting section 331. The first positioning section 332 outputs the thus positioned image as a first positioned image, to the second focusing degree calculation section 335 and the combining section 338.

The second positioning section 333 performs pixel-by-pixel positioning of one image fed from the frame memory 320, with reference to the reference image set by the reference image setting section 331. The one image is a non-reference image out of the two images stored in the frame memory 320. The second positioning section 333 outputs the thus positioned image as a second positioned image, to the third focusing degree calculation section 336 and the combining section 338.

The first focusing degree calculation section 334 calculates a focusing degree of the reference image, pixel by pixel. For example, the first focusing degree calculation section 334 performs high pass filter processing or bandpass filter processing on the image and outputs a processing result as the focusing degree. The first focusing degree calculation section 334 outputs the calculated focusing degree as a first focusing degree to the combination map generation section 337.

The second focusing degree calculation section 335 calculates a focusing degree of the first positioned image, pixel by pixel, and outputs the calculated focusing degree as a second focusing degree to the combination map generation section 337.

The third focusing degree calculation section 336 calculates a focusing degree of the second positioned image, pixel by pixel, and outputs the calculated focusing degree as a third focusing degree to the combination map generation section 337.

Figure 13:
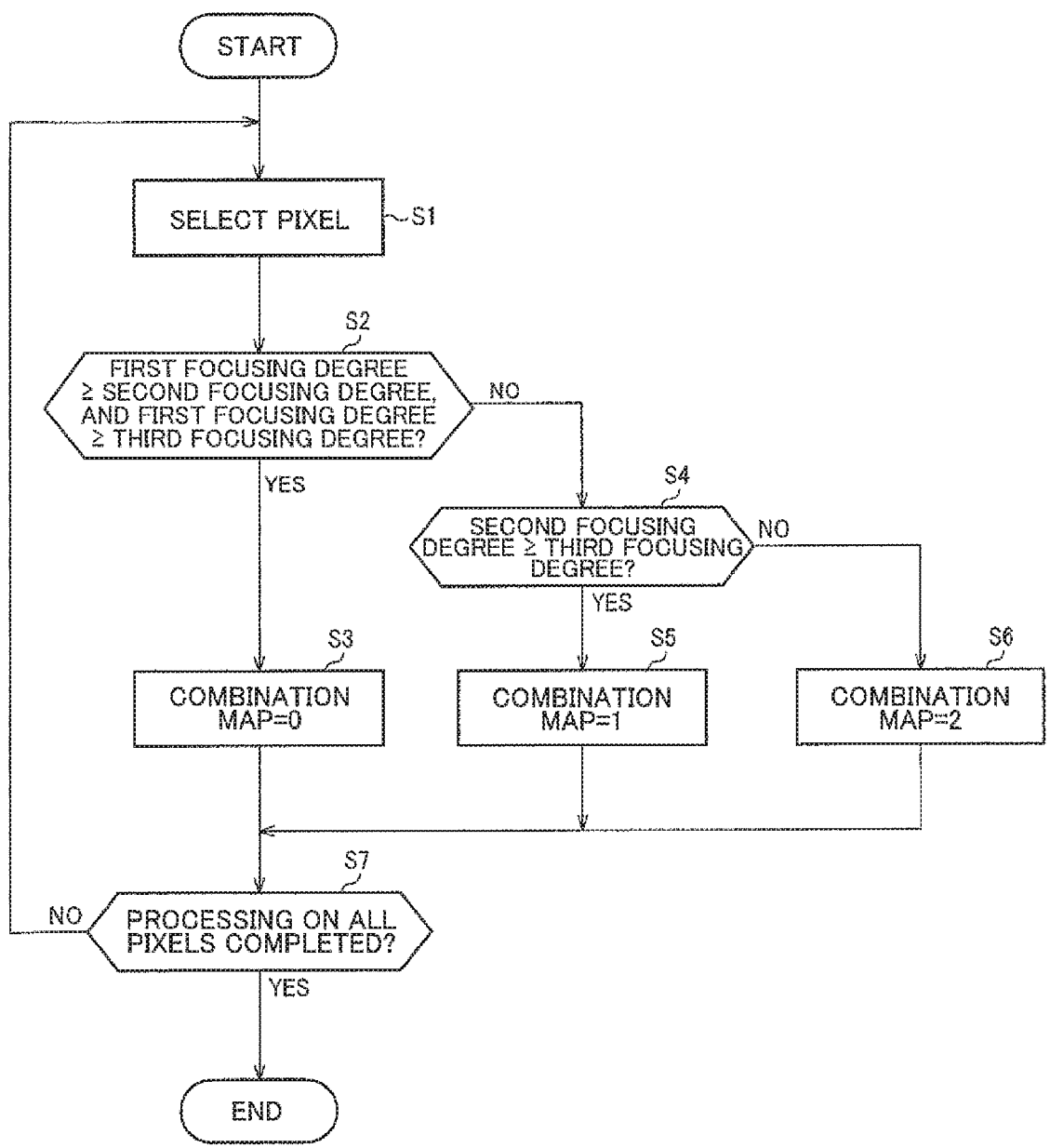
FIG. 13 is a flowchart illustrating a procedure of processing performed by a combination map generation section.

The combination map generation section 337 compares the first to third focusing degrees pixel by pixel, generates a combination map equal in size to the image based on comparison results, and outputs the combination map to the combining section 338. The combination map is a map storing "0", "1", or "2" in each pixel. FIG. 13 is a flowchart illustrating a procedure of processing performed by the combination map generation section 337. In a step S1, the combination map generation section 337 selects one of the pixels included in an image. Subsequently, in a step S2, the combination map generation section 337 determines whether a condition of the first focusing degree≥the second focusing degree and the first focusing degree≥the third focusing degree is satisfied. If the condition in the step S2 is satisfied, the procedure goes to a step S3, and the combination map generation section 337 stores "0" in the pixel of the combination map. If the condition in the step S2 is not satisfied, the procedure goes to a step S4, and the combination map generation section 337 determines whether a condition of the second focusing degree≥the third focusing degree is satisfied. If the condition in the step S4 is satisfied, the procedure goes to a step S5, and the combination map generation section 337 stores "1" in the pixel of the combination map. If the condition in the step S4 is not satisfied, the procedure goes to a step S6, and the combination map generation section 337 stores "2" in the pixel of the combination map.

The combining section 338 combines the reference image, the first positioned image, and the second positioned image based on the combination map. If the value of the pixel of the combination map is "0", the combining section 338 selects a pixel value of the reference image. If the value of the pixel of the combination map is "1", the combining section 338 selects a pixel value of the first positioned image. If the value of the pixel of the combination map is "2", the combining section 338 selects a pixel value of the second positioned image. The combining section 338 performs this selection for all the pixels.

While the description has been given of a case of M=3, a relation of M>4 may hold. That is, the reference image setting section 331 sets one reference image out of (M−1) images stored in the frame memory 320. Operations of the first positioning section 332, the first focusing degree calculation section 334, and the second focusing degree calculation section 335 are as described above. The second positioning section 333 performs pixel-by-pixel positioning of (M−2) images with reference to the reference image, and outputs the thus positioned images as the second to (M−1)th positioned images. The third focusing degree calculation section 336 calculates focusing degrees of the second to (M−1)th positioned images, pixel by pixel, and outputs the calculated focusing degrees as the third to M-th focusing degrees. The combination map generation section 337 compares the first to M-th focusing degrees pixel by pixel, and generates the combination map based on comparison results.

5. Surgery Support System

As the endoscope apparatus, the present disclosure may assume a type in which a scope is connected to a control device and operated by a user to photograph the inside of a body. However, the present disclosure is not limited to this type of endoscope apparatus, and is also assumed to be applicable, for example, to an endoscope apparatus in a surgery support system using a robot.

Such a surgery support system includes, for example, a control device, a robot, and a scope. The scope is, for example, a rigid scope. The control device is a device that controls the robot. That is, the user operates an operation section of the control device to move the robot, and performs surgery on a patient through the robot. In addition, the user operates the operation section of the control device to manipulate the scope through the robot and photograph a surgical region. The control device includes the processing section 300 shown in FIG. 2 or 3. The user operates the robot while seeing images displayed on a display device by the processing section 300. The present disclosure can be applied to the control device in such a surgery support system. The control device may be integrated in the robot.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An imaging device, comprising a processor including hardware, the processor being configured to implement:

controlling a focus position of an objective optical system configured to form an image of a subject on an image sensor;

acquiring L×N images per second captured by the image sensor, where L is an integer of two or greater and N is a number of one or greater; and combining acquired M images into one extended depth of field image to extend a depth of field, where M is an integer greater than N, and outputting L extended depth of field images per second, wherein the processor sets one of the M images as a reference image, performs positioning of the other image or images of the M images with respect to the reference image, and combines the thus positioned M images into the one extended depth of field image.

2. The imaging device as defined in claim 1, wherein the processor sets the focus position at a different focus position, at a timing of capturing each of the M images.

3. The imaging device as defined in claim 2,
wherein the focus position comprises first to M-th focus positions, the first focus position being a focus position at which a farthest subject is in focus, and the M-th focus position being a focus position at which a nearest subject is in focus, and
wherein the processor sets the focus position at any one of the second to (M−1)th focus positions at every other timing of capturing an image.

4. The imaging device as defined in claim 3, wherein N is two, and M is an integer of three or greater and five or less.

5. The imaging device as defined in claim 2,
wherein the focus position comprises first to M-th focus positions, the first focus position being a focus position at which a farthest subject is in focus, and the M-th focus position being a focus position at which a nearest subject is in focus, and
wherein, at a timing of capturing a next image after capturing an image at the first focus position, the processor sets the focus position at any one of the second to (M−1)th focus positions instead of the M-th focus position, and
wherein, at a timing of capturing a next image after capturing an image at the M-th focus position, the processor sets the focus position at any one of the second to (M−1)th focus positions instead of the first focus position.

6. The imaging device as defined in claim 1,
wherein N is an integer, and
wherein, out of acquired first to (M+N)th images, the processor combines the first to M-th images into a first extended depth of field image, and combines the (N+1)th to (M+N)th images into a second extended depth of field image.

7. The imaging device as defined in claim 6, wherein the processor sets any one of the first to N-th images as the reference image when performing the positioning of the first to M-th images.

8. The imaging device as defined in claim 1, wherein provided that the processor has acquired first to (M+p+q)th images,
the processor
combines the first to M-th images into a first extended depth of field image, combines the (p+1)th to (M+p)th images into a second extended depth of field image, and combines the (q+1)th to (M+p+q)th images into a third extended depth of field image, where p and q are integers of one or greater and less than M, and p is not equal to q, and
outputs the L extended depth of field images from the L×N images per second on average.

9. The imaging device as defined in claim 1, wherein a relation of 1<N<2 holds.

10. The imaging device as defined in claim 2,
wherein the processor sets the focus position at any one of first to M-th focus positions at the timing of capturing each image, the first focus position being a focus position at which a farthest subject is in focus, and the M-th focus position being a focus position at which a nearest subject is in focus, and
wherein the processor sets an image captured at any one of the second to (M−1)th focus positions, as the reference image.

11. The imaging device as defined in claim 1, wherein when the M images comprise first to M-th images sequentially captured, the processor sets any one of the second to (M−1)th images as the reference image.

12. The imaging device as defined in claim 1,
wherein N is an integer, and
wherein the processor sets the reference image at intervals of N images.

13. An endoscope apparatus, comprising the imaging device as defined in claim 1.

14. An operation method of an imaging device, comprising:
controlling a focus position of an objective optical system configured to form an image of a subject on an image sensor;
acquiring L×N images per second captured by the image sensor, where L is an integer of two or greater and N is a number of one or greater; and
setting one of acquired M images as a reference image, where M is an integer greater than N, performing positioning of the other image or images of the M images with respect to the reference image, combining the thus positioned M images into one extended depth of field image, and outputting L extended depth of field images per second.

* * * * *